United States Patent
Sharma et al.

(10) Patent No.: US 11,571,193 B2
(45) Date of Patent: *Feb. 7, 2023

(54) METHODS AND DEVICES FOR VEIN HARVESTING

(71) Applicant: Covidien LP, Mansfield, MA (US)

(72) Inventors: Ashish Sharma, Atlanta, GA (US); David N. Heard, Boulder, CO (US); Joe D. Sartor, Longmont, CO (US)

(73) Assignee: COVIDIEN LLP, Mansfield, MA (US)

(*) Notice: Subject to any disclaimer, the term of this patent is extended or adjusted under 35 U.S.C. 154(b) by 362 days.

This patent is subject to a terminal disclaimer.

(21) Appl. No.: 16/845,298

(22) Filed: Apr. 10, 2020

(65) Prior Publication Data

US 2020/0237352 A1 Jul. 30, 2020

Related U.S. Application Data

(63) Continuation of application No. 14/857,956, filed on Sep. 18, 2015, now Pat. No. 10,646,210.

(Continued)

(51) Int. Cl.
*A61B 17/00* (2006.01)
*A61B 8/12* (2006.01)
(Continued)

(52) U.S. Cl.
CPC .......... *A61B 17/00008* (2013.01); *A61B 8/12* (2013.01); *A61B 18/1445* (2013.01);
(Continued)

(58) Field of Classification Search
CPC .......... A61B 17/00008; A61B 18/1445; A61B 2017/00353; A61B 2017/2906; A61B 2017/320044
See application file for complete search history.

(56) References Cited

U.S. PATENT DOCUMENTS

| | | |
|---|---|---|
| 2,011,169 A | 8/1935 | Wappler et al. |
| 2,028,635 A | 1/1936 | Wappler |

(Continued)

FOREIGN PATENT DOCUMENTS

| | | |
|---|---|---|
| DE | 19906260 A1 | 9/1999 |
| EP | 0565822 A2 | 10/1993 |

(Continued)

OTHER PUBLICATIONS

Extended European Search Report for application No. 16180494.3 dated Dec. 23, 2016.

(Continued)

*Primary Examiner* — Sarah A Simpson
(74) *Attorney, Agent, or Firm* — Carter, DeLuca & Farrell LLP

(57) ABSTRACT

A vein harvesting device is disclosed. The vein harvesting device includes a handle assembly, at least one elongated portion, first and second end effectors, and a tip. Each end effector is disposed adjacent a distal portion of the at least one elongated portion. Each end effector includes a first jaw member and a second jaw member, and at least one jaw member is movable toward the other jaw member. The tip is disposed in mechanical cooperation with the elongated portion. A distal end of the tip extends distally beyond a distal-most end of the first end effector. The first end effector is movable independently of the tip, and the second end effector is movable independently of the tip.

17 Claims, 8 Drawing Sheets

Related U.S. Application Data

(60) Provisional application No. 62/063,475, filed on Oct. 14, 2014.

(51) Int. Cl.
*A61B 18/14* (2006.01)
*A61B 17/02* (2006.01)
*A61B 17/32* (2006.01)
*A61B 17/29* (2006.01)
*A61B 18/00* (2006.01)

(52) U.S. Cl.
CPC .............. *A61B 2017/00106* (2013.01); *A61B 2017/00353* (2013.01); *A61B 2017/00902* (2013.01); *A61B 2017/0225* (2013.01); *A61B 2017/2906* (2013.01); *A61B 2017/320044* (2013.01); *A61B 2018/0063* (2013.01); *A61B 2018/00297* (2013.01); *A61B 2018/00428* (2013.01); *A61B 2018/00791* (2013.01); *A61B 2018/00875* (2013.01); *A61B 2018/00982* (2013.01)

(56) References Cited

U.S. PATENT DOCUMENTS

| | | |
|---|---|---|
| 3,659,606 A | 5/1972 | Reimels |
| 3,764,427 A | 10/1973 | Reimels |
| 3,788,325 A | 1/1974 | Jacobsen |
| 4,052,980 A | 10/1977 | Grams et al. |
| 4,528,982 A | 7/1985 | Wellenstam |
| 4,655,217 A | 4/1987 | Reed |
| 5,011,489 A | 4/1991 | Salem |
| 5,013,312 A | 5/1991 | Parins et al. |
| 5,373,840 A | 12/1994 | Knighton |
| 5,395,384 A | 3/1995 | Duthoit et al. |
| 5,522,827 A | 6/1996 | Combs et al. |
| 5,571,172 A | 11/1996 | Chin |
| 5,591,183 A | 1/1997 | Chin |
| 5,593,418 A | 1/1997 | Mollenauer |
| 5,601,581 A | 2/1997 | Fogarty et al. |
| 5,601,589 A | 2/1997 | Fogarty et al. |
| 5,607,441 A | 3/1997 | Sierocuk et al. |
| 5,653,722 A | 8/1997 | Kieturakis |
| 5,658,282 A | 8/1997 | Daw et al. |
| 5,667,480 A | 9/1997 | Knight et al. |
| 5,676,636 A | 10/1997 | Chin |
| 5,690,668 A | 11/1997 | Fogarty et al. |
| 5,695,514 A | 12/1997 | Chin |
| 5,702,417 A | 12/1997 | Hermann |
| 5,707,382 A | 1/1998 | Sierocuk et al. |
| 5,716,325 A | 2/1998 | Bonutti |
| 5,722,934 A | 3/1998 | Knight et al. |
| 5,725,479 A | 3/1998 | Knight et al. |
| 5,730,748 A | 3/1998 | Fogarty et al. |
| 5,738,628 A | 4/1998 | Sierocuk et al. |
| 5,759,150 A | 6/1998 | Konou et al. |
| 5,762,604 A | 6/1998 | Kieturakis |
| 5,772,576 A | 6/1998 | Knighton et al. |
| 5,782,753 A | 7/1998 | DeFonzo et al. |
| 5,782,854 A | 7/1998 | Hermann |
| 5,797,946 A | 8/1998 | Chin |
| 5,797,947 A | 8/1998 | Mollenauer |
| 5,800,540 A | 9/1998 | Chin |
| 5,803,903 A | 9/1998 | Athas et al. |
| 5,814,059 A | 9/1998 | Hart et al. |
| 5,814,060 A | 9/1998 | Fogarty et al. |
| 5,817,013 A * | 10/1998 | Ginn ............... A61B 1/0014 600/101 |
| 5,823,946 A | 10/1998 | Chin |
| 5,827,318 A | 10/1998 | Bonutti |
| 5,836,945 A | 11/1998 | Perkins |
| D403,066 S | 12/1998 | DeFonzo |
| 5,843,104 A | 12/1998 | Samuels |
| 5,853,417 A | 12/1998 | Fogarty et al. |
| RE36,043 E | 1/1999 | Knighton |
| 5,871,496 A | 2/1999 | Ginn et al. |
| 5,873,889 A | 2/1999 | Chin |
| 5,876,413 A | 3/1999 | Fogarty et al. |
| 5,891,140 A | 4/1999 | Ginn et al. |
| 5,893,858 A | 4/1999 | Spitz |
| 5,893,866 A | 4/1999 | Hermann et al. |
| 5,895,353 A | 4/1999 | Lunsford et al. |
| 5,899,912 A | 5/1999 | Eaves, III |
| 5,899,913 A | 5/1999 | Fogarty et al. |
| 5,902,315 A | 5/1999 | DuBois |
| 5,902,316 A | 5/1999 | Mollenauer |
| 5,913,818 A | 6/1999 | Co et al. |
| 5,913,866 A | 6/1999 | Ginn et al. |
| 5,913,870 A | 6/1999 | DeFonzo et al. |
| 5,916,233 A | 6/1999 | Chin |
| 5,922,004 A | 7/1999 | DuBois |
| 5,928,135 A | 7/1999 | Knight et al. |
| 5,928,138 A | 7/1999 | Knight et al. |
| 5,938,680 A | 8/1999 | Ginn |
| 5,944,734 A | 8/1999 | Hermann et al. |
| 5,951,584 A | 9/1999 | Hermann |
| 5,968,065 A | 10/1999 | Chin |
| 5,968,066 A | 10/1999 | Fogarty et al. |
| 5,970,982 A | 10/1999 | Perkins |
| 5,972,010 A | 10/1999 | Taheri |
| 5,976,168 A | 11/1999 | Chin |
| 5,979,452 A | 11/1999 | Fogarty et al. |
| 5,980,549 A | 11/1999 | Chin |
| 5,984,937 A | 11/1999 | Morse et al. |
| 5,993,384 A | 11/1999 | Lunsford et al. |
| 5,993,472 A | 11/1999 | Hermann et al. |
| 6,004,340 A | 12/1999 | Hermann et al. |
| 6,013,090 A | 1/2000 | Fogarty et al. |
| 6,019,771 A | 2/2000 | Bennett et al. |
| 6,022,313 A | 2/2000 | Ginn et al. |
| 6,030,396 A | 2/2000 | Samuels |
| 6,030,406 A | 2/2000 | Davis et al. |
| 6,036,713 A | 3/2000 | Kieturakis |
| 6,036,714 A | 3/2000 | Chin |
| 6,042,538 A | 3/2000 | Puskas |
| 6,051,013 A | 4/2000 | Mollenauer |
| 6,059,802 A | 5/2000 | Ginn |
| 6,068,639 A | 5/2000 | Fogarty et al. |
| 6,071,232 A | 6/2000 | Knighton et al. |
| 6,077,289 A | 6/2000 | Mollenauer |
| 6,080,102 A | 6/2000 | Konou et al. |
| 6,110,170 A | 8/2000 | Taylor et al. |
| 6,129,661 A | 10/2000 | Iafrati et al. |
| 6,139,489 A | 10/2000 | Wampler et al. |
| 6,143,008 A | 11/2000 | Eaves, III |
| 6,162,173 A | 12/2000 | Chin et al. |
| 6,174,313 B1 | 1/2001 | Bonutti |
| 6,176,825 B1 | 1/2001 | Chin et al. |
| 6,193,651 B1 | 2/2001 | DeFonzo |
| 6,193,653 B1 | 2/2001 | Evans et al. |
| 6,196,968 B1 | 3/2001 | Rydin et al. |
| 6,203,557 B1 | 3/2001 | Chin |
| 6,203,559 B1 | 3/2001 | Davis et al. |
| 6,206,823 B1 | 3/2001 | Kolata et al. |
| 6,206,899 B1 | 3/2001 | Ginn |
| 6,228,024 B1 | 5/2001 | Co et al. |
| 6,240,924 B1 | 6/2001 | Fogarty et al. |
| 6,264,670 B1 | 7/2001 | Chin |
| 6,277,137 B1 | 8/2001 | Chin |
| 6,283,963 B1 | 9/2001 | Regula |
| 6,319,265 B1 | 11/2001 | Ginn |
| 6,322,499 B1 | 11/2001 | Evans et al. |
| 6,348,037 B1 | 2/2002 | Chin et al. |
| 6,350,236 B1 | 2/2002 | Hipps et al. |
| 6,375,665 B1 | 4/2002 | Nash et al. |
| 6,413,208 B1 | 7/2002 | Schollhorn et al. |
| 6,428,468 B1 | 8/2002 | Knighton et al. |
| 6,428,556 B1 | 8/2002 | Chin |
| 6,432,044 B1 | 8/2002 | Lunsford et al. |
| 6,436,116 B1 | 8/2002 | Spitz et al. |
| 6,436,118 B1 | 8/2002 | Kayan |
| 6,443,159 B1 | 9/2002 | Fogarty et al. |
| 6,443,970 B1 | 9/2002 | Schulze et al. |

(56) References Cited

U.S. PATENT DOCUMENTS

| | | |
|---|---|---|
| 6,447,529 B2 | 9/2002 | Fogarty et al. |
| 6,451,035 B1 | 9/2002 | Fogarty et al. |
| 6,453,906 B1 | 9/2002 | Taylor et al. |
| 6,454,784 B1 | 9/2002 | Mollenauer |
| 6,468,206 B1 | 10/2002 | Hipps et al. |
| 6,482,153 B1 | 11/2002 | Hipps et al. |
| 6,506,200 B1 | 1/2003 | Chin |
| 6,511,494 B1 | 1/2003 | Knighton et al. |
| 6,527,771 B1 * | 3/2003 | Weadock ......... A61B 17/00008 606/171 |
| 6,527,787 B1 | 3/2003 | Fogarty et al. |
| 6,551,335 B1 | 4/2003 | Bardeau et al. |
| 6,572,615 B2 | 6/2003 | Schulze et al. |
| 6,592,582 B2 | 7/2003 | Hess et al. |
| 6,592,604 B2 | 7/2003 | Hess et al. |
| 6,596,010 B1 | 7/2003 | Hermann et al. |
| 6,607,547 B1 | 8/2003 | Chin |
| 6,616,661 B2 | 9/2003 | Wellman et al. |
| 6,623,482 B2 | 9/2003 | Pendekanti et al. |
| 6,648,815 B2 | 11/2003 | Schoellhorn et al. |
| 6,652,521 B2 | 11/2003 | Schulze |
| 6,656,176 B2 | 12/2003 | Hess et al. |
| 6,660,016 B2 | 12/2003 | Lindsay |
| 7,566,300 B2 | 7/2009 | Devierre |
| 7,645,289 B2 | 1/2010 | Bayer |
| 10,646,210 B2 | 5/2020 | Sharma et al. |
| 2003/0195544 A1 | 10/2003 | Hess et al. |
| 2003/0212420 A1 | 11/2003 | Gruhl et al. |
| 2005/0096670 A1 | 5/2005 | Wellman et al. |
| 2008/0255589 A1 * | 10/2008 | Blakeney ............ A61B 17/1285 606/142 |
| 2010/0036198 A1 * | 2/2010 | Tacchino ................ A61B 17/29 600/106 |

FOREIGN PATENT DOCUMENTS

| | | |
|---|---|---|
| WO | 9939632 A1 | 8/1999 |
| WO | 03000139 A1 | 1/2003 |
| WO | 03013365 A1 | 2/2003 |
| WO | 03013367 A2 | 2/2003 |

OTHER PUBLICATIONS

EP Office Action for EP 02744699 dated Apr. 6, 2009.
Extended European Search Report for Application No. 15189623 dated Mar. 17, 2016.
European Examination Report for application No. 15 189 623.0 dated Jun. 7, 2018 (5 pages).

* cited by examiner

METHODS AND DEVICES FOR VEIN HARVESTING

CROSS REFERENCE TO RELATED APPLICATIONS

This application is a continuation of U.S. patent application Ser. No. 14/857,956, filed on Sep. 18, 2015, which claims the benefit of and priority to U.S. Provisional Patent Application Ser. No. 62/063,475, filed on Oct. 14, 2014, the entire disclosures of each of which are incorporated by reference herein.

BACKGROUND

Technical Field

The present disclosure relates to methods and devices for endoscopic surgery, in particular to methods and devices for dissecting tissue to create a working space for endoscopic instruments.

Background of Related Art

Numerous surgical procedures have been developed to replace veins and arteries that have become blocked by disease. As a result of aging and/or disease, veins and arteries may become blocked by plaque deposits, stenosis, or cholesterol. In some instances, these blockages can be treated with artherectomy, angioplasty or stent placement, and coronary bypass surgery is not required. Coronary bypass surgery is required when these other methods of treatment cannot be used or have failed to clear the blocked vein or artery. In the coronary bypass surgery, a vein is harvested from elsewhere in the body and grafted into place (e.g., between the aorta and the coronary artery) beyond the point of blockage.

The coronary bypass surgery requires a length of vein or artery for the graft. It is preferred to use a vein taken from the patient undergoing the bypass surgery. The patient is a ready source of suitable veins that will not likely be rejected by the body after transplantation and grafting onto the aorta and coronary artery. The saphenous vein in the leg is often the best substitute for small veins or arteries such as the coronary arteries, and it is often the preferred vein for use in coronary bypass surgery. This is because the saphenous vein is typically 3 to 5 mm in diameter, about the same size as the coronary arteries. Also, the venous system of the legs is sufficiently redundant so that after removal of the saphenous vein, other veins that remain in the leg are adequate to provide adequate blood flow. The cephalic vein in the arm is an alternative that is sometimes used.

In a typical operation previously required to harvest the saphenous vein, the surgeon cut into the leg to allow access to the saphenous vein and cut the vein from the leg. To expose the vein, the surgeon makes a series of incisions from the groin to the knee or the ankle leaving one or more skin bridges along the line of the incisions. (Some surgeons make one continuous incision from the groin to the knee or ankle). Handling of the vein must be kept to a minimum, but the vein must be removed from connective tissue, which requires some force. After exposing the vein, the surgeon grasps it with his fingers while stripping off the surrounding tissues with dissecting scissors or other scraping instruments. The surgeon uses his fingers and blunt dissection tools to pull and lift (or mobilize) the vein from the surrounding tissue. The vein is mobilized or pulled as far as possible through each incision. To reach under the skin bridges, the surgeon lifts the skin with retractors and digs the vein free. While stripping the vein, the surgeon will encounter the various tributary veins that feed into the saphenous vein. These tributaries must be ligated and divided. To divide and ligate tributaries that lie under the skin bridges, the surgeon may need to cut one end of the saphenous vein and pull it under the skin bridge to gently pull the vein out from under the skin bridge until the tributary is sufficiently exposed so that it may be ligated and divided. When the vein has been completely mobilized, the surgeon cuts the proximal and distal ends of the vein and removes the vein from the leg. After removal, the vein is prepared for implantation into the graft site, and the long incisions made in the leg are stitched closed.

The procedure described above can also be used to harvest veins for a femoral popliteal bypass, in which an occluded femoral artery is bypassed from above the occlusion to the popliteal artery above or below the knee. The procedure can also be used to harvest veins for the revascularization of the superior mesenteric artery which supplies blood to the abdominal cavity and intestines. In this case, the harvested vein is inserted between the aorta to the distal and patent (unblocked) section of the mesenteric artery. For bypass grafts of the lower popliteal branches in the calf, the procedure can be used to harvest the umbilical vein. The harvested vein can also be used for a vein loop in the arm (for dialysis) between the cephalic vein and brachial artery. The procedures may be used also to harvest veins for femoral-tibial, femora-peroneal, aorto-femoral, and iliac-femoral bypass operations and any other bypass operation.

As can be seen from the description of the harvesting operation, the harvesting operation is very traumatic in its own right. In the case of coronary artery bypass, this operation is carried out immediately before the open chest operation required to graft the harvested vein onto the coronary arteries. The vein harvesting operation is often the most troublesome part of the operation. The long incisions created in the leg can be slow to heal and very painful. Complications resulting from the vein harvesting operation can also hinder the patient's recovery from the entire operation.

Additionally, during the harvesting of the saphenous vein, it is often desirable to leave as much of the pedicle (i.e., between about 4 mm and about 5 mm of perivascular fat surrounding the vein) preserved as possible. The preservation of the pedicle helps the saphenous vein remain uninjured during surgery, and also helps the long-term patency and viability of the saphenous vein. For instance, following the surgery, the pedicle acts as a natural sheath to help prevent the saphenous vein from getting unnaturally distended due to higher arterial pressures.

The method of vein harvesting presented herein is accomplished with endoscopic procedures while preserving much of the pedicle. This allows the vein to be harvested in an operation that requires only a few small incisions, and increases the patency of the vein. Endoscopic surgical techniques for operations such as gall bladder removal and hernia repair are now common. The surgeon performing the operation makes a few small incisions and inserts long tools, including forceps, scissors, and staplers into the incision and deep into the body. Viewing the tools through an endoscope, or a video display from an endoscope, the surgeon can perform all the cutting and suturing operations necessary for a wide variety of operations. The procedures are also referred to as endoscopic surgery, laparoscopic surgery, minimally invasive surgery, or video-assisted surgery. References to endoscopic surgery and endoscopes below is intended to encompass all of these fields, and all operations described below with reference to endoscopes can also be accomplished with laparoscopes, gastroscopes, and any other imaging devices which may be conveniently used.

Minimally invasive procedures for vein removal have been proposed. Knighton, Endoscope and Method for Vein Removal, U.S. Pat. No. 5,373,840 shows a method of cutting the saphenous vein at one end, and grasping the vein with graspers or forceps, then sliding a ring over the vein while securing the vein at the same time. Knighton uses a dissecting tool with an annular cutting ring, and requires that the saphenous vein be overrun or progressively surrounded with the dissecting tool and the endoscope, so that after the endoscope has been inserted as far as it will go, the entire dissected portion of the vein has been pulled in the lumen of the endoscope. As shown in FIGS. 1 and 10 of Knighton, the method requires deployment of the forceps inside the annular dissection loop, and it requires deployment of the loop and graspers inside the endoscope lumen. The blood vessel must be cut and grasped by the forceps before it can be dissected by the dissecting ring.

SUMMARY

The present disclosure relates to a vein harvesting device, comprising a handle assembly, at least one elongated portion extending distally from the handle assembly, a first end effector, a second end effector, and a tip. The first end effector is disposed adjacent a distal portion of the at least one elongated portion. The first end effector includes a first jaw member and a second jaw member. At least one jaw member is movable toward the other jaw member. The second end effector is disposed adjacent a distal portion of the elongated portion(s). The second end effector includes a first jaw member and a second jaw member, at least one of which is movable toward the other jaw member. The tip is disposed in mechanical cooperation with the elongated portion. A distal end of the tip extends distally beyond a distal-most end of the first end effector. The first end effector is movable independently of the tip, and the second end effector is movable independently of the tip.

In disclosed aspects, the at least one elongated portion includes a first elongated portion and a second elongated portion. Each of the first and second elongated portions extends distally from the handle assembly. The first end effector is disposed adjacent a distal portion of the first elongated portion. The second end effector is disposed adjacent a distal portion of the second end effector.

In disclosed aspects, the tip is configured to bluntly dissect tissue.

In disclosed aspects, the tip defines a hollow cavity, and each of the first end effector and the second end effector is housed at least partially within the hollow cavity.

In disclosed aspects, the tip is either transparent or translucent.

In disclosed embodiments, each of the first end effector and the second end effector is configured to seal tissue.

In disclosed aspects, the vein harvesting device also includes a band disposed in mechanical cooperation with the first end effector and the second end effector. The band is configured to extend between the end effectors and to contact a portion of a vein between the end effectors. Here, it is disclosed that one lateral end of the band is removably coupled to the first end effector.

In disclosed aspects, the vein harvesting device also includes an ultrasound probe disposed on at least one of the first end effector, the second end effector, the tip, and the elongated portion.

In disclosed aspects, the at least one elongated portion includes a first elongated portion and a second elongated portion. Each of the first and second elongated portions extends distally from the handle assembly. The first end effector is disposed adjacent a distal portion of the first elongated portion. The second end effector is disposed adjacent a distal portion of the second end effector. The tip is configured to bluntly dissect tissue. The tip defines a hollow cavity therein, and each of the first end effector and the second end effector is housed at least partially within the hollow cavity.

The present disclosure also relates to a method of endoscopically harvesting the saphenous vein and surrounding pedicle. The method comprises using a vein harvesting device including a handle assembly, at least one elongated portion extending distally from the handle assembly, a first end effector disposed adjacent a distal portion of the at least one elongated portion, a second end effector disposed adjacent a distal portion of the at least one elongated portion, and a tip. The first end effector includes a first jaw member and a second jaw member. At least one jaw member is movable toward the other jaw member. The second end effector is disposed adjacent a distal portion of the at least one elongated portion. The second end effector includes a first jaw member and a second jaw member. At least one jaw member is movable toward the other jaw member. The tip is disposed in mechanical cooperation with the elongated portion. A distal end of the tip extends distally beyond a distal-most end of the first end effector.

The method also includes endoscopically inserting at least a portion of the vein harvesting device adjacent the saphenous vein of a patient, bluntly dissecting tissue adjacent the saphenous vein with the tip of the vein harvesting device, sealing and/or cutting tissue surrounding the pedicle with the first end effector of the vein harvesting device, sealing and/or cutting tissue surrounding the pedicle with the second end effector of the vein harvesting device, and removing at least a portion of the saphenous vein and pedicle from the patient.

In disclosed aspects, the method further includes determining the location of the portion of the vein harvesting device using an ultrasound probe.

In disclosed aspects of the method, sealing and/or cutting tissue surrounding the pedicle with the first end effector is done at the same time as sealing and/or cutting tissue surrounding the pedicle with the second end effector.

BRIEF DESCRIPTION OF THE DRAWINGS

Various embodiments of the surgical devices are described herein with reference to the drawings wherein.

DETAILED DESCRIPTION

Figure 1:
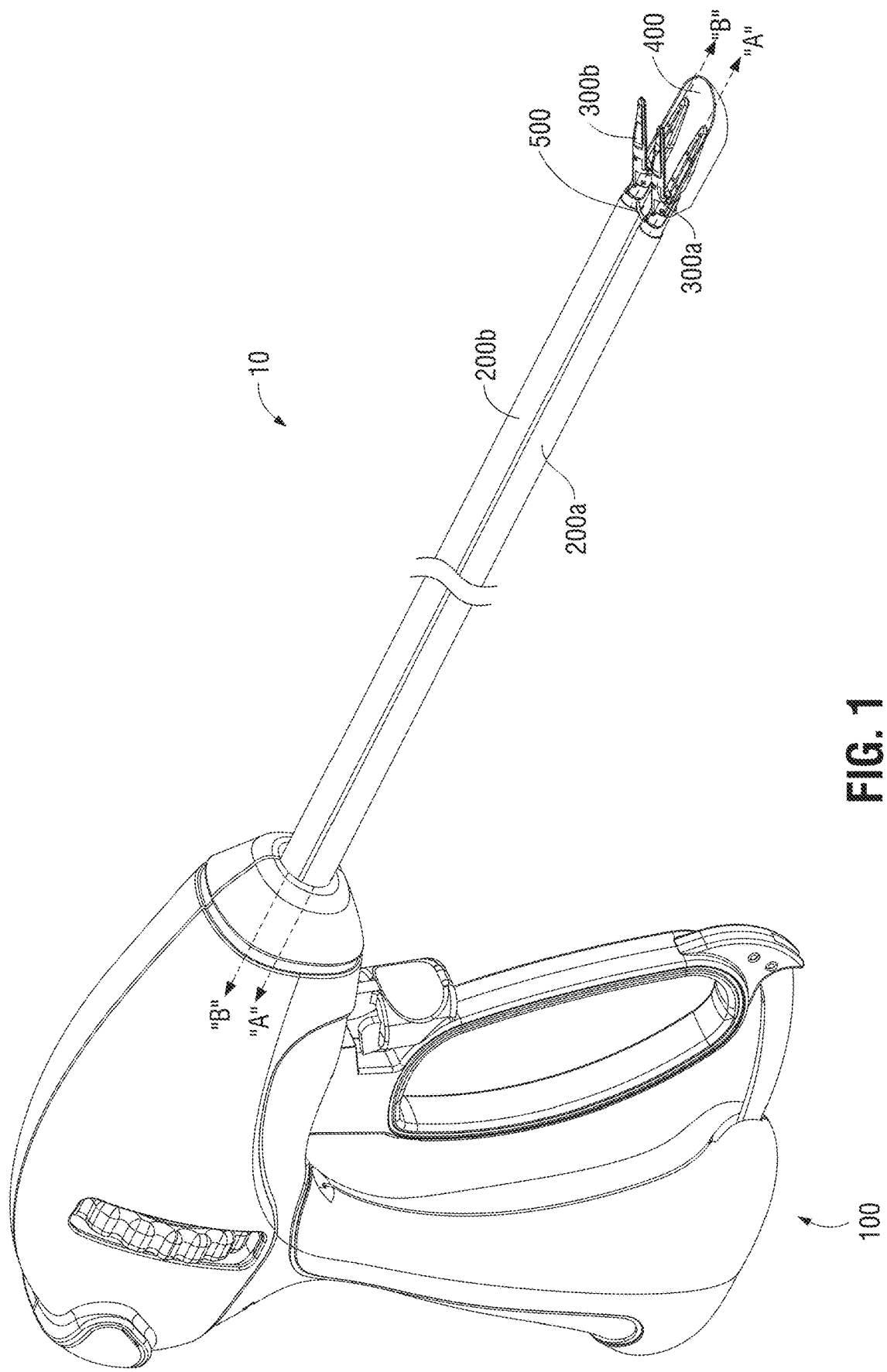
FIG. 1 illustrates a vein harvesting device in accordance with embodiments of the present disclosure.

Embodiments of the presently disclosed vein harvesting device are described in detail with reference to the drawings, in which like reference numerals designate identical or corresponding elements in each of the several views. As used herein the term "distal" refers to that portion of the vein harvesting device that is farther from the user, while the term "proximal" refers to that portion of the vein harvesting device that is closer to the user.

The saphenous vein has a number of tributary veins that carry venous blood into the vein. These tributaries are typically tied off and/or cut off of the saphenous vein before the saphenous vein can be removed. In medical terms, these tributaries must be ligated and divided. When a tributary or side branch is encountered, the surgeon can use endoscopic and laparoscopic tools, for example, to close the tributaries and cut them from the saphenous vein. The tributaries can be separated from the vein after the entire vein is stripped, or the surgeon may choose to separate them as they are encountered.

Referring initially to FIGS. 1-5B, one embodiment of a vein harvesting device 10 is shown for use with various surgical procedures and generally includes a handle assembly 100, a first elongated (e.g., endoscopic) portion 200a extending distally from handle assembly 100 and defining a first longitudinal axis "A-A," and a second elongated (e.g., endoscopic) portion 200b extending distally from handle assembly 100 and defining a second longitudinal axis "B-B." The first end effector 300a is disposed adjacent a distal portion of first elongated portion 200a, the second end effector 300b is disposed adjacent a distal portion of second elongated portion 200b, and a tip 400 is disposed adjacent first and second end effectors 300a, 300b. Vein harvesting device 10 is configured to efficiently remove at least portions of a target vein "V" (e.g., the saphenous vein) while also removing pedicle (i.e., the facial layer surrounding the vein "V") to help the viability of the vein "V" after transplantation thereof. Additionally, vein harvesting device 10 is configured to be used endoscopically, e.g., to reduce the chances of infection.

Tip or blunt dissection tip 400 extends distally of end effectors 300a, 300b and is configured to dissect (e.g., bluntly dissect) or scrape tissue away from the target vein "V" as tip 400 is advanced distally, e.g., while maintaining at least a portion of the pedicle. As shown in FIGS. 1-5B, it is envisioned that tip 400 is scoop-like in shape, defining a hollow cavity 404 therein. The scoop-like shape of tip 400 is configured to scrape tissue away from the target vein "V" and away from end effectors 300a, 300b disposed at least partially within cavity 404. Additionally, it is envisioned that at least a portion of the tip 400 (e.g., the entirety of tip 400) is transparent or translucent. As can be appreciated, the transparency or translucency of tip 400 facilitates the viewing of target tissue and the vein "V" by a surgeon or an endoscope, and allows light to shine through tip 400 to illuminate the target tissue and the vein "V."

Handle assembly 100 is configured to control actuation of end effectors 300a, 300b. Actuation of end effectors 300a, 300b includes opening and approximating of at least a first jaw member 310a, 310b with respect to a second jaw member 320a, 320b, cutting tissue held between first member 310a, 310b and respective second jaw member 320a, 320b, and sealing/fusing tissue held between the first member 310a, 310b and respective second jaw member 320a, 320b by applying energy thereto. Details of a surgical instrument including a handle assembly for controlling actuation of a single end effector can be found in U.S. patent application Ser. No. 10/179,863 (now U.S. Pat. No. 7,101,371) and Ser. No. 10/116,944 (now U.S. Pat. No. 7,083,618), the entire contents of which being incorporated by reference. It is envisioned that handle assembly 100 of the present disclosure can control actuation of end effectors 300a, 300b together, or individually, e.g., via a three-way rocker switch (not explicitly shown). The dual end effectors 300a, 300b are configured to dissect tissue (e.g., side branches "SB" of the saphenous vein) away from the pedicle along two dissection planes (i.e., each dissection plane being defined by a single end effector 300a, 300b). As can be appreciated, the dissection along two planes may result in a faster procedure with respect to dissection along a single plane using a single end effector.

It is further disclosed that first jaw members 310a, 310b are pivotable and that second jaw members 320a, 320b are fixed. Here, it is disclosed that second jaw members 320a, 320b are fixed in a plane "T," defined by a lower surface 402 of tip (see FIG. 3), and that first jaw members 310a, 310b are pivotable. In such embodiments, longitudinal advancement of end effectors 300a, 300b and tip 400 within tissue is facilitated; otherwise, the lower or second jaw members 320a, 320b may protrude beyond plane "T" and impede longitudinal advancement within tissue. It is further envisioned that first jaw members 310a, 310b may be fixed and that second jaw members 320a, 320b are pivotable.

Figure 3:
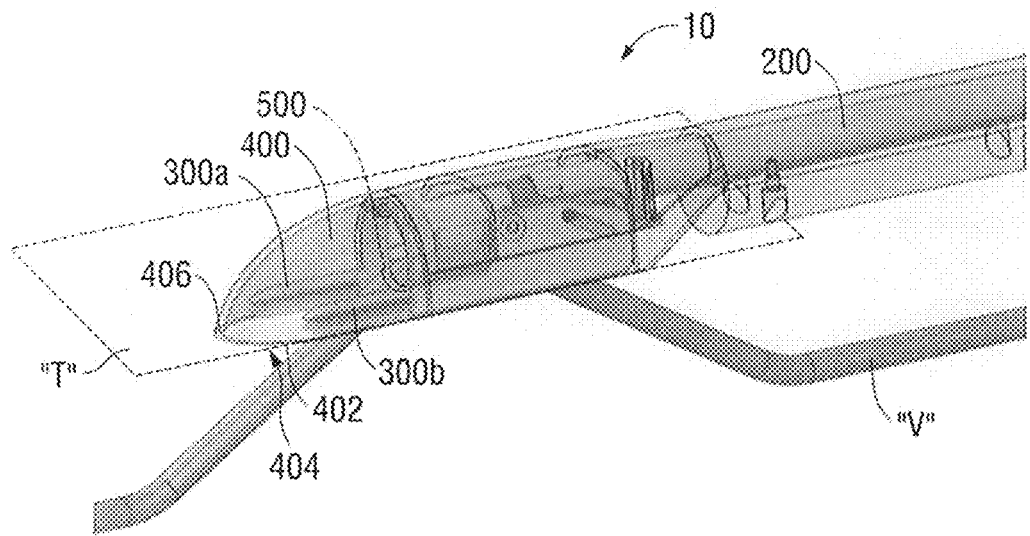
FIGS. 3 and 4 are perspective views of a distal end of the vein harvesting device of FIGS. 1 and 2 shown in engagement with a vein.
Figure 4:
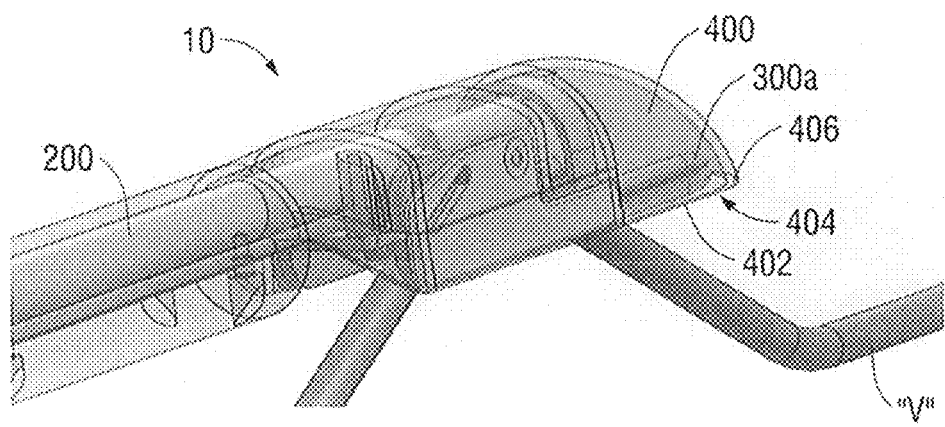

Additionally, and as shown in the embodiment illustrated in FIGS. 3 and 4, disclosed embodiments of vein harvesting device 10 include a single elongated portion 200 having first and second end effectors 300a, 300b extending distally therefrom.

End effectors 300a, 300b and tip 400 are rotatable about axes "A-A" and "B-B," respectively, with respect to endoscopic portions 200a and 200b (or single endoscopic portion 200) and/or with respect to handle assembly 100. Endoscopic portions 200a and 200b (or single endoscopic portion 200) are rotatable about axes "A-A" and "B-B," with respect to handle assembly 100. Accordingly, end effectors 300a, 300b can be rotated within tissue to access all of the tissue/side branches "SB" surrounding the vein "V" without needing to remove end effectors 300a, 300b from within the patient.

It is further disclosed that the distance "D" between end effectors 300a, 300b (i.e., the distance perpendicular to axes "A-A" and "B-B") is configured to be larger than the width of the patient's target vein "V" (e.g., saphenous vein). Moreover, it is disclosed that distance "D" is the width of the vein "V" plus about 2 mm to 3 mm of buffer space on each lateral side of the vein "V." That is, if a patient's vein "V" is 6 mm, it is envisioned that the distance "D" is between about 10 mm and about 12 mm (i.e., 6 mm+2 mm (first lateral side)+2 mm (second lateral side)=10 mm; 6 mm+3 mm (first lateral side)+3 mm (second lateral side)=12 mm). It is further envisioned that a surgeon can choose between various vein harvesting devices 10, which include a different distance "D", based on the actual size of a particular patient's target vein "V." Alternatively, the distance "D" may be variable using one or more dials, gears, spacers, levers, etc. associated with an actuator (not shown) to accomplish this purpose.

Embodiments of vein harvesting device 10 of the present disclosure also include an endoscope disposed between elongated portions 200a, 200b. It is envisioned that the distal end of the endoscope is located proximally of a distal-most end 406 of tip 400 and/or proximally of at least a majority of end effectors 300a, 300b. As noted above, tip 400 is transparent or translucent to allow the endoscope to view the tissue/vein "V" disposed distally of tip 400.

It is further envisioned that vein harvesting device 10 includes a hollow cavity between elongated portions 200a, 200b (or beneath single elongated portion 200). The hollow cavity extends along at least a portion of the length of elongated portions 200a, 200b and is configured to releasably house the patient's vein "V" during the surgical procedure. That is, a surgeon may thread the vein "V" under a band 500, through a distal opening of the hollow cavity, through the hollow cavity, and/or out a proximal opening of the hollow cavity. The use of such a hollow cavity may help the surgeon isolate the vein "V" to help ensure the separated portion of vein "V" does not interfere with the portions of the vein "V" that have yet to be separated from the surrounding tissue.

Figure 2:
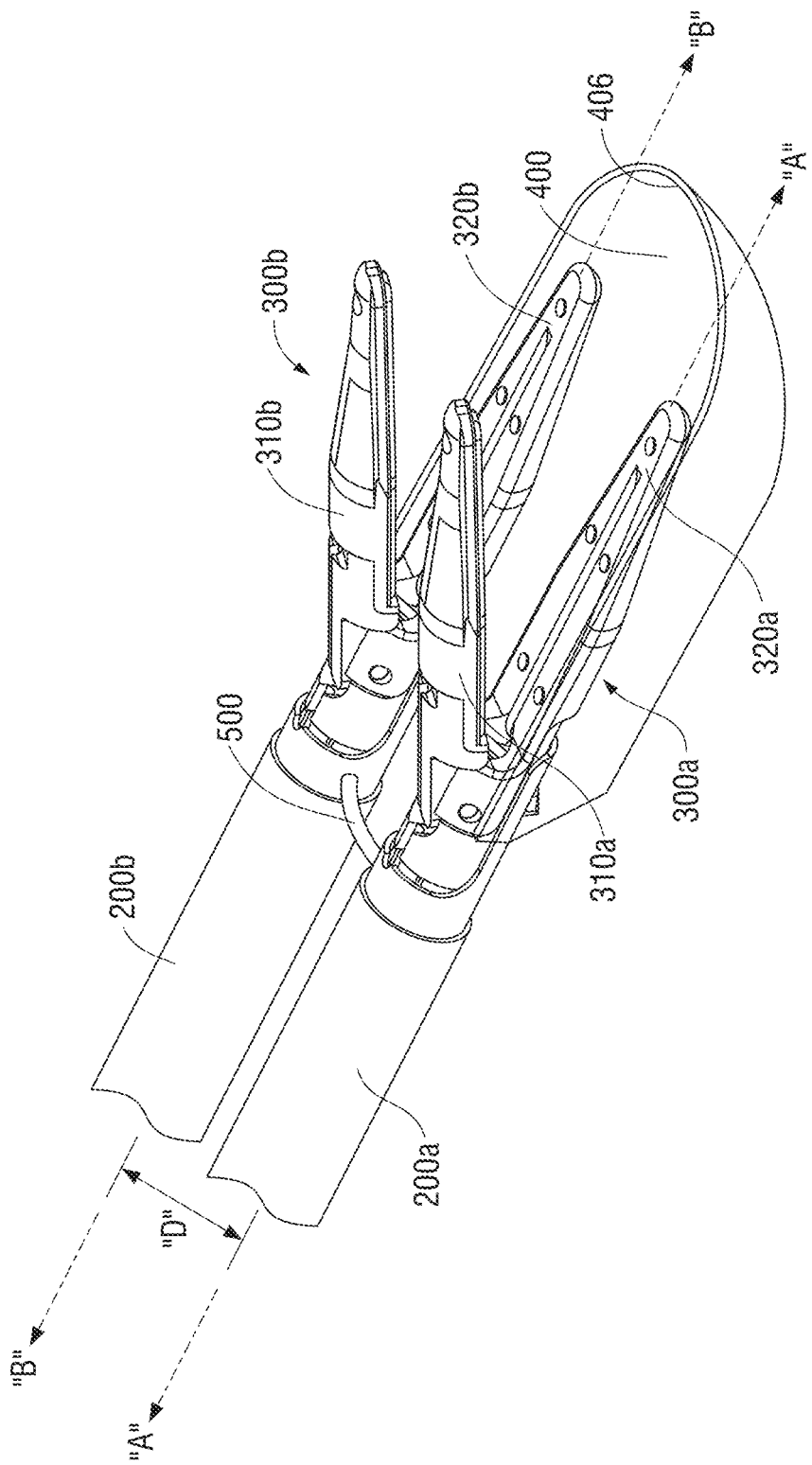
FIG. 2 is a perspective view of a distal end of the vein harvesting device of FIG. 1.
Figure 5A:
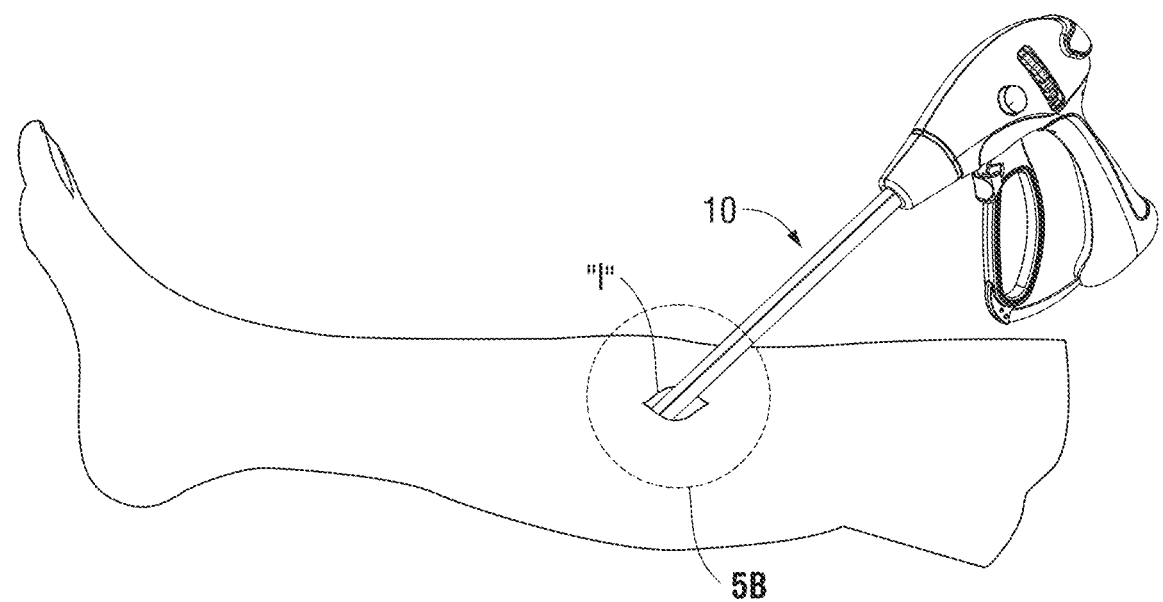
FIG. 5A illustrates the vein harvesting device of FIGS. 1-4 with its distal end within a patient.
Figure 5B:
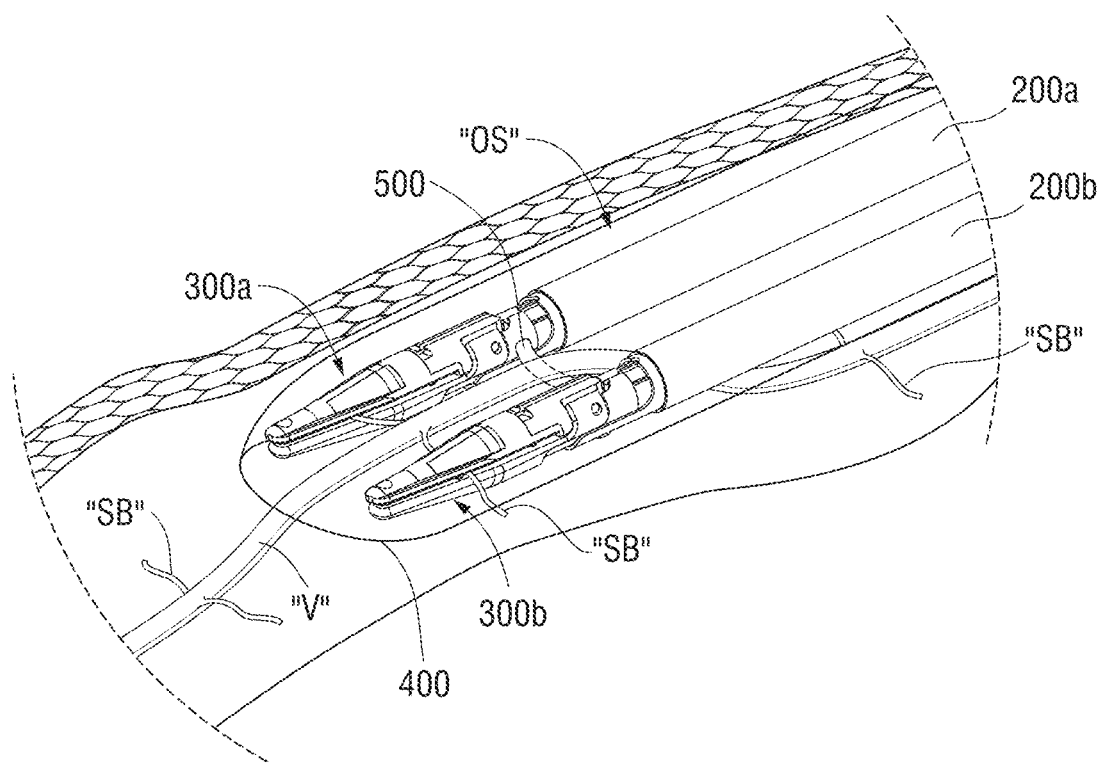
FIG. 5B illustrates the distal end of the vein harvesting device of FIGS. 1-5A within the patient.
Figure 6:
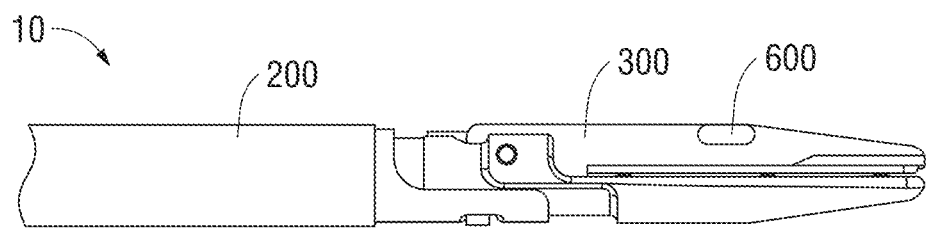
FIG. 6 is a schematic side view of a distal end of a vein harvesting device according with embodiments of the present disclosure, and which includes an ultrasound probe.

Referring now to FIGS. 2 and 5B, vein harvesting device 10 is shown having band 500 extending between proximal portions of end effectors 300a and 300b. In FIG. 5A, the incision "I" is shown enlarged for clarity. In FIG. 5B, the operating space "OS" is shown enlarged for clarity. Band 500 (e.g., a non-traumatic, flexible silastic band) is configured to hold, maintain or retract the target vein "V" (e.g., including pedicle) of a patient "P" away from the distal end of vein harvesting device 10 so as not to interfere with an end effector 300 or end effectors 300a, 300b that may be accessing tissue. It is further disclosed that at least one lateral side of band 500 is removably coupled to the adjacent end effector 300a, 300b. In such embodiments, the surgeon may remove one of the lateral ends of band 500 from end effector 300a, 300b (e.g., via a separate instrument), wrap that portion of band 500 around the target vein "V," and then move the removed lateral end of band 500 back into engagement with end effector 300a, 300b, such that the vein "V" is secured between end effectors 300 and 300b, as shown in FIG. 5B. It is envisioned that the removable coupling of a lateral end of band 500 is accomplished by threading/unthread/tying/untying that portion of band 500 through/to an aperture and/or hook on end effector 300a and/or 300b.

It is further envisioned that band 500 can be deployed and/or retracted with the use of a control (e.g., switch) on handle assembly 100. Band 500 may initially lie parallel with either first elongated portion 200a or second elongated portion 200b. Here, band 500 can be deployed, e.g., by a switch, to hold, maintain or retract the target vein "V" and surrounding perivascular fat (e.g., pedicle "P") by orienting band 500 in an axis perpendicular to the "A" and "B" axes. It is envisioned that band 500 can be reset back into its original position by using the same switch.

It is also disclosed that band 500 (e.g., disposed in a different suitable location) holds the vein "V" either between elongated portions 200a and 200b or adjacent a single elongated portion 200a or 200b. It is also disclosed that band 500 is used with vein harvesting device 10 having a single elongated portion 200.

During vein harvesting procedures when a surgeon does not have access to the disclosed vein harvesting device 10 or band 500, the surgeon often either uses his or her finger or hand to hold back the vein "V," or the surgeon uses a separate instrument including a hook, for example. However, during vein harvesting inclusive of pedicle harvesting, as described herein, the size and weight of the vein/pedicle (as compared to a skeletonized vein without pedicle) impede the use of a finger, hand or hook to hold back the vein/pedicle. Accordingly, band 500 of the present disclosure is especially useful during harvesting of the vein and pedicle.

With reference to FIGS. 6-8B, another embodiment of vein harvesting device 10 is shown according to embodiments of the present disclosure. Here, vein harvesting device 10 includes an ultrasound probe 600. In the illustrated embodiments, ultrasound probe 600 is disposed adjacent a distal end of vein harvesting device 10 (e.g., on or near end effector 300, or near tip 400 (not illustrated in FIGS. 6-8B for clarity), etc.). The inclusion of ultrasound probe 600 enables a surgeon to determine the exact location of the particular portion of vein harvesting device 10 with respect to the target vein "V." Traditional endoscopic vein harvesting systems rely on direct visualization of the skeletonized vein by means of an endoscopic camera, for example. However, relying on an endoscopic camera to harvest the vein inclusive of the pedicle is difficult because the vein "V" is often hidden inside the fascia.

Figure 7A:
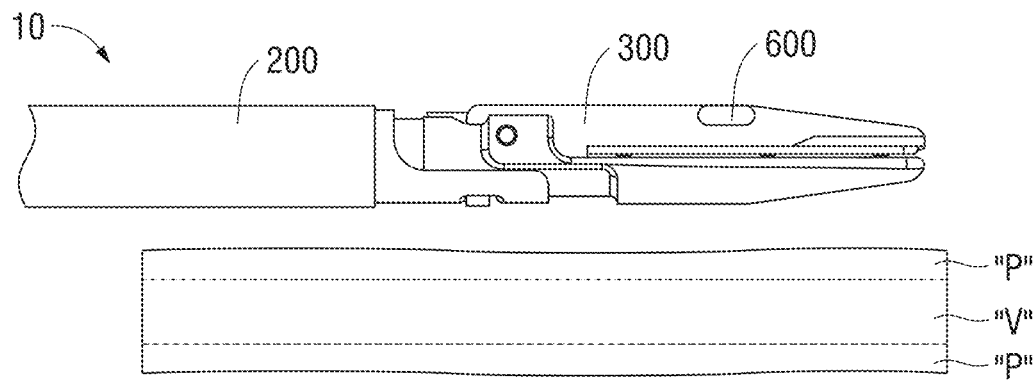
FIGS. 7A and 7B are schematic side and front views, respectively, of the vein harvesting device of FIG. 6 located adjacent a saphenous vein and adjacent pedicle.
Figure 7B:
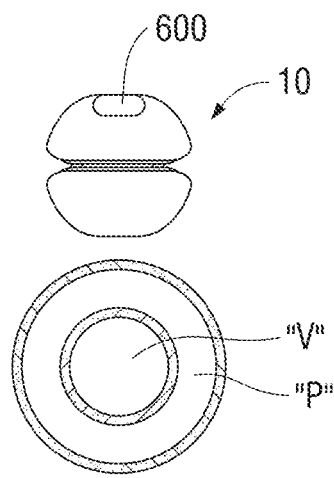

With particular reference to FIGS. 7A and 7B, schematic side and front views, respectively, show vein harvesting device 10 adjacent a saphenous vein "V" and adjacent pedicle "P," which radially surrounds the vein "V." Here, when a surgeon is attempting to remove pedicle "P" along with the vein "V," the use of ultrasound probe 600 facilitates this removal by helping the surgeon determine the precise location of the distal end, for instance, of vein harvesting device 10 with respect to the vein "V."

Figure 8A:
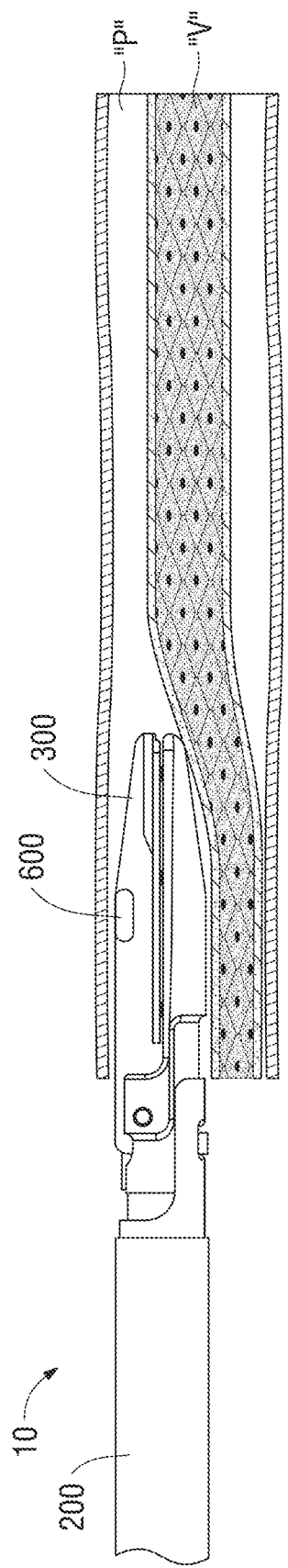
FIGS. 8A and 8B are schematic side and front views, respectively, of a vein harvesting device located adjacent the saphenous vein and located within the pedicle.
Figure 8B:
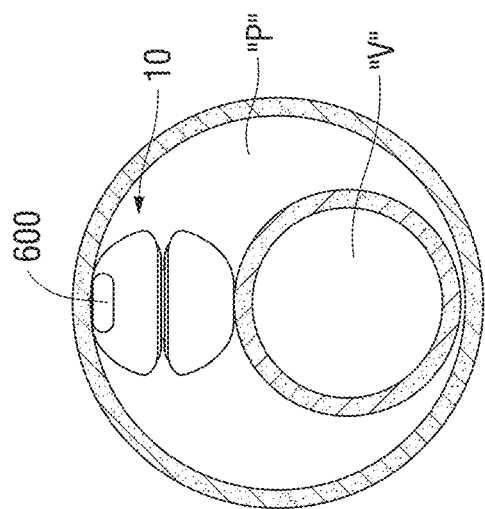

With particular reference to FIGS. 8A and 8B, schematic side and front views, respectively, show vein harvesting device 10 adjacent a saphenous vein "V" and located within pedicle "P." Here, when a surgeon is attempting to remove the vein "V" and not the pedicle "P" (i.e., skeletonized vein removal), it is easier for the surgeon directly view the skeletonized vein with an endoscopic camera, for instance, since the vein "V" is has been separated from the surrounding fascia or pedicle.

The present disclosure also includes methods of performing vein harvesting operations using vein harvesting device 10 discussed herein, and methods of manufacturing vein harvesting device 10 discussed herein.

Methods and devices presented herein take advantage of laparoscopic procedures to lessen the trauma of vein harvesting operations. Instead of making an incision along or over the entire length, or essentially the entire length of the vein "V" to be harvested, the procedure may be conducted with only a few small incisions or a single incision. All that is needed is a working space large enough to allow the surgeon to use vein harvesting device 10 and view the operation through a laparoscope, for example. In disclosed embodiments of the method, the surgeon creates a working space under the skin and over the saphenous vein using laparoscopic techniques. The surgeon makes one or several small incisions to expose the saphenous vein. These incisions are referred to as cut-downs. A distal incision near the knee and/or a proximal incision at the groin are contemplated. If the entire length of the saphenous vein is to be harvested, an additional incision can be made close to the ankle. The saphenous vein can be seen through the cut-downs. The use of three or four incisions used to harvest the entire saphenous vein are merely a matter of convenience, and those particularly skilled in laparoscopic procedures may require fewer incisions, and also more small incisions may be desired.

After the incision(s), the surgeon inserts vein harvesting device 10 into one incision and pushes it along the saphenous vein "V" towards the other incision. The tunneling creates a channel running along the saphenous vein "V." The channel may be expanded by insertion of a balloon (not shown), which can be inflated to expand or propagate the tunnel further along the saphenous vein "V."

A balloon (not shown) may packed inside vein harvesting device 10. The balloon is a non-elastomeric balloon or bladder and may be deployed through a balloon trocar extending along at least a portion of the length of vein harvesting device 10. It is disclosed that when used for tunneling along the saphenous vein "V," the balloon is approximately 60 centimeters long, and the balloon trocar may be between about 10-20 centimeters long. The balloon can be expanded by injecting liquid or gas into the balloon through an inflation port. Sterile saline solution is an example of an inflation medium for medical applications. Alternately, air, $CO_2$, or even foam or other substances may be injected to cause inflation. Further details of the balloon and its use for harvesting veins are disclosed in U.S. patent application Ser. No. 12/550,462 (now U.S. Pat. No. 8,133,248), the entire contents of which being incorporated by reference herein.

Figure 9A:
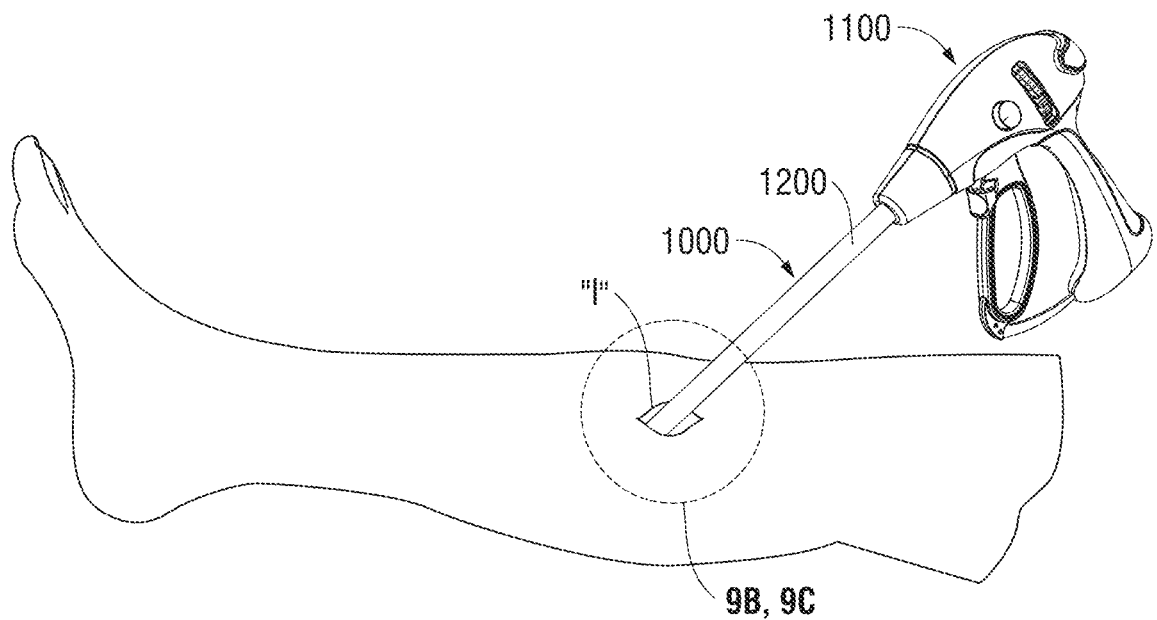
FIG. 9A illustrates a vein harvesting device with its distal end within a patient in accordance with embodiments of the present disclosure.
Figure 9B:
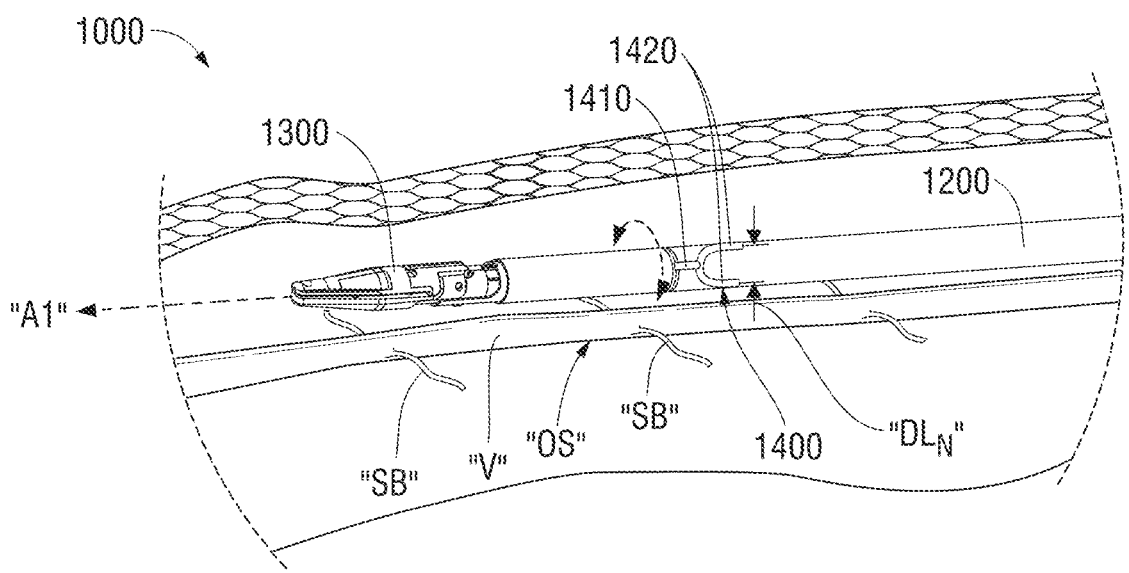
FIG. 9B illustrates the distal portion of the vein harvesting device of FIG. 9A including a retractor shown in a non-deployed position and FIG. 9C illustrates the distal portion of the vein harvesting device of FIGS. 9A and 9B showing the retractor in a deployed position.
Figure 9C:
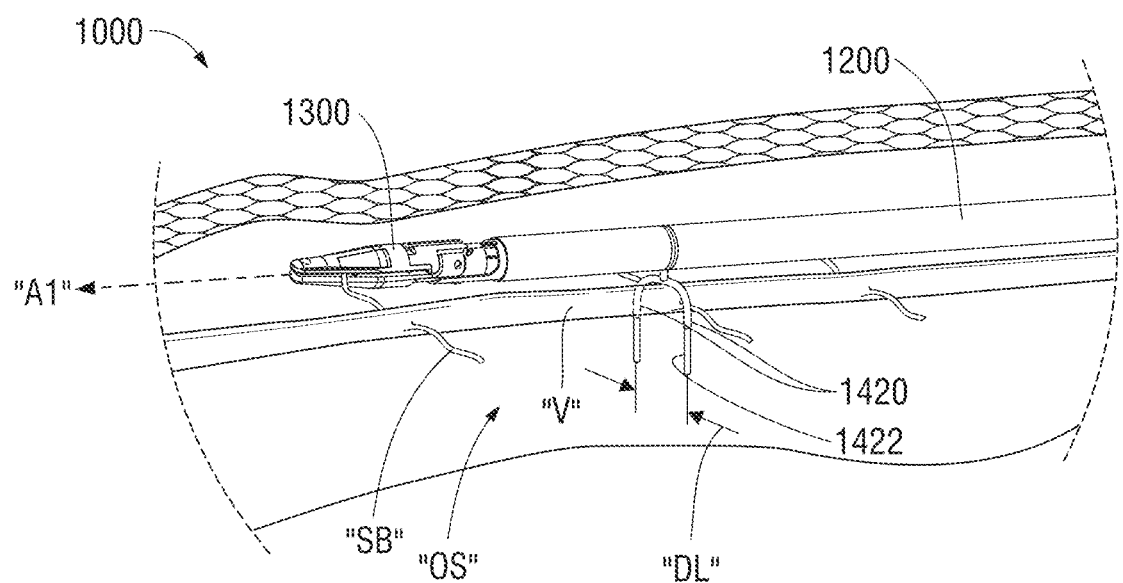

With reference to FIGS. 9A-9C, a vein harvesting device according to embodiments of the present disclosure is shown, and is referenced by numeral 1000. Vein harvesting device 1000 is configured to assist in the endoscopic removal of a patient's vein "V" (e.g., the saphenous vein) and surrounding pedicle "P." For clarity, the incision "I" in FIG. 9A, and the operating space "OS" in FIGS. 9B and 9C are shown enlarged.

Vein harvesting device 1000 includes a handle assembly 1100, an elongated portion 1200 extending distally from handle assembly 1100, an end effector 1300 disposed adjacent a distal end of elongated portion 1200, and a deployable retractor 1400 disposed in mechanical cooperation with elongated portion or endoscopic portion 1200. Handle assembly 1100 is configured to control actuation of end effector 1300 (e.g., pivoting at least one jaw member with respect to the other, and cutting and sealing tissue disposed between the jaw members). Details of a surgical instrument including a handle assembly for controlling actuation of an end effector can be found in U.S. patent application Ser. No. 10/179,863 (now U.S. Pat. No. 7,101,371) and Ser. No. 10/116,944 (now U.S. Pat. No. 7,083,618), the entire contents of which have been incorporated by reference herein.

Additionally, handle assembly 1100 is configured to control deployment of retractor 1400 between a first, non-deployed position where a shaft 1410 is aligned with a longitudinal axis "A1-A1" defined by elongated portion 1200 (FIG. 9B), to a deployed position where shaft 1410 is disposed at an angle (e.g., a right angle) with respect to the longitudinal axis "A1-A1" (FIG. 9C). Any suitable controls may be included (e.g., on handle assembly 1100) to control deployment of retractor 1400, such as a rotatable knob, a switch, a pivotable handle, etc.

In use, when retractor 1400 is deployed (FIG. 9C), retractor 1400 is used to keep portions of the vein "V" (e.g., the saphenous vein) and pedicle "P" away from end effector 1300. For instance, retractor 1400 is used to keep the portions of the vein "V" and pedicle "P" that have already been separated from surrounding tissue/side branches "SB" away from end effector 1300. As can be appreciated, keeping portions of the vein "V" and pedicle "P" away from end effector 1300 helps protect these portions of the vein "V" and pedicle "P" from inadvertent contact with the jaw members, and helps facilitate the sealing and cutting of additional tissue/side branches "SB."

Retractor 1400 includes the shaft 1410 and a pair of legs 1420, which form a U-like shape. Legs 1420 extend from shaft 1410 and are sized to hold portions of the vein "V" and pedicle "P" therebetween. As such, it is envisioned that the distance "DL" between legs 1420 is between about 10 mm and about 15 mm, however the distance "DL" between legs 1420 may be larger or smaller.

Additionally, since it is often desirable in endoscopic surgery to have elongated portion 1200 with a diameter of less than 10 mm, legs 1420 of retractor 1400 may be formed from a shape memory material. Here, when retractor 1400 is in its non-deployed position (FIG. 9B), the distance "$DL_N$" between legs 1420 is equal to or less than the diameter of elongated portion 1200. In disclosed embodiments, when retractor 1400 moves toward its deployed position (FIG. 9C), legs 1420 spring open to increase the distance "DL" therebetween.

Additionally, the retractor 1400 may be at least partially disposed within a recess of elongated portion 1200 when retractor 1400 is in its non-deployed position, such that the profile of elongated portion 1200 is substantially unchanged by the inclusion of retractor 1400. That is, in such embodiments, retractor 1400 would not increase the overall diameter or profile of elongated portion 1200 (e.g., endoscopic portion), and thus would not hinder the endoscopic use of vein harvesting device 1000.

It is further disclosed that at least portions of retractor 1400 include a non-traumatic tissue-contacting surface. For example, at least an inner surface 1422 of legs 1420 may include a non-traumatic material disposed thereon to help prevent damage to the vein "V" or pedicle "P."

Additionally, in disclosed embodiments, retractor 1400 is rotatable about longitudinal axis "A-A," defined by elongated portion. The retractor 1400 may be rotatable about longitudinal axis "A-A" independently of rotation of end effector 1300, which may also be rotatable about longitudinal axis "A-A." Rotation of retractor 1400 may be accomplished by the rotation of a knob 1430 located in mechanical cooperation with handle assembly 1100. Knob 1430 may be mechanically linked to the portion of shaft 1410 that extends from elongated portion 1200.

The various embodiments disclosed herein may also be configured to work with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the instruments disclosed herein, while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different (smaller or larger) than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of various embodiments. Those skilled in the art will envision other modifications within the scope and spirit of the claims appended hereto.

What is claimed is:

1. A vein harvesting device, comprising:
   a first elongated portion;
   a second elongated portion;
   a first end effector disposed adjacent a distal portion of the first elongated portion, the first end effector including a first jaw member and a second jaw member, at least one jaw member movable toward the other jaw member;
   a second end effector disposed adjacent a distal portion of the second elongated portion, the second end effector including a first jaw member and a second jaw member, at least one jaw member of the second end effector movable toward the other jaw member of the second end effector; and
   a band extending between the first end effector and the second end effector and configured to contact a portion of a vein between the first end effector and the second end effector, the band configured for direct contact with the first end effector and the second end effector simultaneously, the band deployable between a first position wherein the band is disposed at a first angle relative to the first elongated portion and a second position wherein the band is disposed at a second angle relative to the first elongated portion, the first angle being different from the second angle.

2. The vein harvesting device according to claim 1, wherein the first angle is parallel to the first elongated portion.

3. The vein harvesting device according to claim 2, wherein the second angle is perpendicular to the first elongated portion.

4. The vein harvesting device according to claim 1, wherein a lateral end of the band is removably coupled to the first end effector.

5. The vein harvesting device according to claim 1, wherein a lateral end of the band is fixedly coupled to one of the first end effector or the second end effector.

6. The vein harvesting device according to claim 1, further comprising a tip operatively connected to the first elongated portion, a distal end of the tip extending distally beyond a distal-most end of the first end effector, the tip is fixed from pivotal movement relative to the first elongated portion.

7. The vein harvesting device according to claim 6, wherein the first end effector is fixed from longitudinal movement relative to the tip, and wherein the second end effector is fixed from longitudinal movement relative to the tip.

8. The vein harvesting device according to claim 7, wherein the first end effector is movable independently of the tip, and wherein the second end effector is movable independently of the tip.

9. The vein harvesting device according to claim 6, wherein the tip is configured to bluntly dissect tissue and defines a hollow cavity therein, and wherein each of the first end effector and the second end effector is housed at least partially within the hollow cavity.

10. The vein harvesting device according to claim 1, wherein the band is configured to support the vein such that a proximal portion of the vein is disposed proximally of the band, and a distal portion of the vein is disposed distally of the band.

11. A vein harvesting device, comprising:
    a first elongated portion;
    a second elongated portion;
    a first end effector disposed adjacent a distal portion of the first elongated portion, the first end effector including a first jaw member and a second jaw member, at least one jaw member movable toward the other jaw member;
    a second end effector disposed adjacent a distal portion of the second elongated portion, the second end effector including a first jaw member and a second jaw member, at least one jaw member of the second end effector movable toward the other jaw member of the second end effector; and
    a band configured to extend between the first end effector and the second end effector and configured to contact a portion of a vein between the first end effector and the second end effector, a lateral end of the band is removably coupled to the first end effector, the band deployable between a first position wherein the band is disposed at a first angle relative to the first elongated portion and a second position wherein the band is disposed at a second angle relative to the first elongated portion, the first angle being different from the second angle.

12. The vein harvesting device according to claim 11, wherein the first angle is parallel to the first elongated portion, and wherein the second angle is perpendicular to the first elongated portion.

13. The vein harvesting device according to claim 11, further comprising a tip operatively connected to the first elongated portion, a distal end of the tip extending distally beyond a distal-most end of the first end effector, the tip is fixed from pivotal movement relative to the first elongated portion.

14. A vein harvesting device, comprising:
   a first elongated portion;
   a second elongated portion;
   a first end effector disposed adjacent a distal portion of the first elongated portion, the first end effector including a first jaw member and a second jaw member, at least one jaw member movable toward the other jaw member;
   a second end effector disposed adjacent a distal portion of the second elongated portion, the second end effector including a first jaw member and a second jaw member, at least one jaw member of the second end effector movable toward the other jaw member of the second end effector; and
   a band configured to extend between the first end effector and the second end effector and configured to contact a portion of a vein between the first end effector and the second end effector, wherein a lateral end of the band is fixedly coupled to one of the first end effector or the second end effector.

15. The vein harvesting device according to claim 14, wherein the band is deployable from a first position where the band is disposed at a first angle relative to the first elongated portion to a second position where the band is disposed at a second angle relative to the first elongated portion, wherein the first angle is different from the second angle.

16. The vein harvesting device according to claim 14, wherein the first angle is parallel to the first elongated portion, and wherein the second angle is perpendicular to the first elongated portion.

17. The vein harvesting device according to claim 14, further comprising a tip operatively connected to the first elongated portion, a distal end of the tip extending distally beyond a distal-most end of the first end effector, the tip is fixed from pivotal movement relative to the first elongated portion.

* * * * *